United States Patent
Boyle et al.

(10) Patent No.: US 10,690,681 B2
(45) Date of Patent: Jun. 23, 2020

(54) METHODS TO DETECT MYOCARDIAL INJURY AND USES THEREOF

(71) Applicant: Washington University, St. Louis, MO (US)

(72) Inventors: Walter A. Boyle, St. Louis, MO (US); Richard Bach, St. Louis, MO (US)

(73) Assignee: Washington University, St. Louis, MO (US)

( * ) Notice: Subject to any disclaimer, the term of this patent is extended or adjusted under 35 U.S.C. 154(b) by 77 days.

(21) Appl. No.: 15/062,759

(22) Filed: Mar. 7, 2016

(65) Prior Publication Data

US 2016/0258965 A1 Sep. 8, 2016

Related U.S. Application Data

(60) Provisional application No. 62/129,484, filed on Mar. 6, 2015.

(51) Int. Cl.
*G01N 33/53* (2006.01)
*G01N 33/68* (2006.01)

(52) U.S. Cl.
CPC ........ *G01N 33/6887* (2013.01); *G01N 2333/4712* (2013.01); *G01N 2800/32* (2013.01); *G01N 2800/56* (2013.01)

(58) Field of Classification Search
CPC ........... G01N 33/6887; G01N 2800/56; G01N 2333/4712; G01N 2800/32
See application file for complete search history.

(56) References Cited

U.S. PATENT DOCUMENTS

| | | | | |
|---|---|---|---|---|
| 2008/0057590 A1* | 3/2008 | Urdea | ................. | G01N 33/74 436/71 |
| 2008/0261242 A1* | 10/2008 | Goix | ................. | G01N 21/6428 435/7.21 |
| 2010/0159491 A1* | 6/2010 | Hess | ................. | G01N 33/6893 435/7.93 |
| 2012/0156702 A1* | 6/2012 | Mayr | ................. | G01N 33/6887 435/7.92 |
| 2013/0130403 A1 | 5/2013 | Goix et al. | | |
| 2014/0045714 A1 | 2/2014 | Gerszten et al. | | |
| 2014/0213638 A1* | 7/2014 | Bowles | ................. | A61K 38/00 514/44 R |

FOREIGN PATENT DOCUMENTS

| | | | |
|---|---|---|---|
| WO | 1996032648 A1 | 10/1996 | |
| WO | 2002023191 A1 | 3/2002 | |
| WO | 2004059293 A2 | 7/2004 | |
| WO | WO2013169890 | * 11/2013 | ............. G01N 33/53 |

OTHER PUBLICATIONS

Mair et al (Coronary Artery Disease 1994;5:865-872).*
Muscle injury panel rat kit (2010 retrieved from https://www.mesoscale.com/~/media/files/product%20inserts/muscle%20injury%20panel%201%20rat%20k0040075.pdf).*
Berna et al. (Anal. Chem. 2007, 79, 4199-4205).*
Boyle, W. et al., "Early Biomarkers of Myocardial Injury," International Anesthesia Research Society, Abstract, 2015, p. S-122, 1 pg., vol. 120.
Boyle, W. et al., "Early Biomarkers of Myocardial Injury," International Anesthesia Research Society, Poster, undated, 1 pg., No. 2262.
De Groot, M. et al., "Measurement of myocardial infarct size from plasma fatty acid-binding protein or myoglobin, using individually estimated clearance rates," Cardiovascular Res., 1999, pp. 315-324, vol. 44, Elsevier Science B.V.
Ishii, J. et al., "Serum concentrations of myoglobin vs human heart-type cytoplasmic fatty acid-binding protein in early detection of acute myocardial infarction," Clinical Chemistry, 1997, pp. 1372-1378, vol. 43, No. 8.

\* cited by examiner

*Primary Examiner* — Julie Wu
*Assistant Examiner* — Carmencita M Belei
(74) *Attorney, Agent, or Firm* — Polsinelli PC

(57) ABSTRACT

The present invention provides an accurate and reliable method to detect acute cardiovascular syndromes or disorders and to detect acute cardiovascular syndromes or disorders at earlier time points such that more aggressive interventions can be used in high risk subjects

11 Claims, 9 Drawing Sheets
(8 of 9 Drawing Sheet(s) Filed in Color)

METHODS TO DETECT MYOCARDIAL INJURY AND USES THEREOF

CROSS REFERENCE TO RELATED APPLICATIONS

This application claims the benefit of U.S. Provisional Application No. 62/129,484, filed Mar. 6, 2015, the disclosure of which is hereby incorporated by reference in its entirety.

FIELD OF THE INVENTION

The present invention provides an accurate and reliable method to detect acute cardiovascular syndromes or disorders and to detect acute cardiovascular syndromes or disorders at earlier time points such that more aggressive interventions can be used in high risk subjects

BACKGROUND OF THE INVENTION

Cardiac disease and acute myocardial injury (AMI) remain a leading cause of preventable mortality in the US. Detection of acute myocardial injury (AMI) remains challenging, particularly as it relates to identification of patients with significant evolving AMI events that could benefit most from early use of invasive approaches. Cardiac specific biomarkers have the potential to help distinguish high risk groups. The cardiac troponins now widely used to specifically identify AMI events typically rise slowly following AMI, and very small elevations which are now detectable early with high sensitivity assays can be nonspecific and difficult to interpret.

Therefore, there is a need in the art to develop an accurate and reliable method to detect AMI and to detect AMI at earlier time points such that more aggressive interventions can be used in high risk subjects.

SUMMARY OF THE INVENTION

In an aspect, the disclosure provides a method to detect acute cardiovascular syndrome or disorder in a subject, the method comprising: detecting a level of cardiac troponin I (cTnI), fatty acid binding protein (FABP3) and ventricular myosin alkali light chain (MYL3) in a biological sample obtained from the subject; comparing the level of cTnI, FABP3 and MYL3 detected in (a) to a reference level; and detecting an acute cardiovascular syndrome or disorder when the level of cTnI, FABP3 and MYL3 is significantly increased relative to the reference level.

In another aspect, the disclosure provides A method to determine the time that has elapsed since onset of an acute cardiovascular syndrome or disorder in a subject, the method comprising: detecting a level of cardiac troponin I (cTnI), fatty acid binding protein (FABP3) and ventricular myosin alkali light chain (MYL3) in a biological sample obtained from the subject at about time 0, about time 30 min and about time 60 minutes; comparing the levels of cTnI, FABP3 and MYL3 detected at about time 0, about time 30 min and about time 60 minutes; and detecting the time that has elapsed since onset of the acute cardiovascular syndrome or disorder, wherein: (i) a very early period (<1 hour) is detected by low cTnI levels, a positive rate of change and a positive change in the rate of change in cTnI, a positive rate of change and a positive change in the rate of change in FABP3, and a positive then negative rate of change and change in the rate of change in MYL3; (ii) an early period (<4 hours) is detected by a positive rate of change and a positive change in the rate of change in cTnI, a positive rate of change in FABP3, and a positive then negative change in the rate of change in FABP3; and (iii) a later period (>8 hours) is detected by high cTnI levels, a negative rate of change in cTnI and an absent rate of change and change in rate of change in FABP3 and MYL3.

In still another aspect, the disclosure provides a method to differentiate between a large and a small acute myocardial injury (AMI) in a subject, the method comprising: detecting a level of cardiac troponin I (cTnI), fatty acid binding protein (FABP3) and ventricular myosin alkali light chain (MYL3) in a biological sample obtained from the subject at about time 0, about time 30 min and about time 60 minutes; comparing the levels of cTnI, FABP3 and MYL3 detected at about time 0, about time 30 min and about time 60 minutes; and detecting a large AMI when the cTnI levels at 16-24 hours are greater than about 20 ng/ml and/or when the FABP3 levels are significantly elevated compared to a reference level and/or when the rate of change of cTnI and/or FABP3 are significantly elevated compared to a reference level.

BRIEF DESCRIPTION OF THE FIGURES

The application file contains at least one drawing executed in color. Copies of this patent application publication with color drawing(s) will be provided by the Office upon request and payment of the necessary fee.

FIG. 2A depicts $d[x]/dt$ and $d^2[x]/dt^2$ at early timepoints (0-8 hours) and FIG. 2B depicts $[x]/dt$ and $d^2[x]/dt^2$ at later timepoints (0-48 hours).

DETAILED DESCRIPTION OF THE INVENTION

Figure 1:
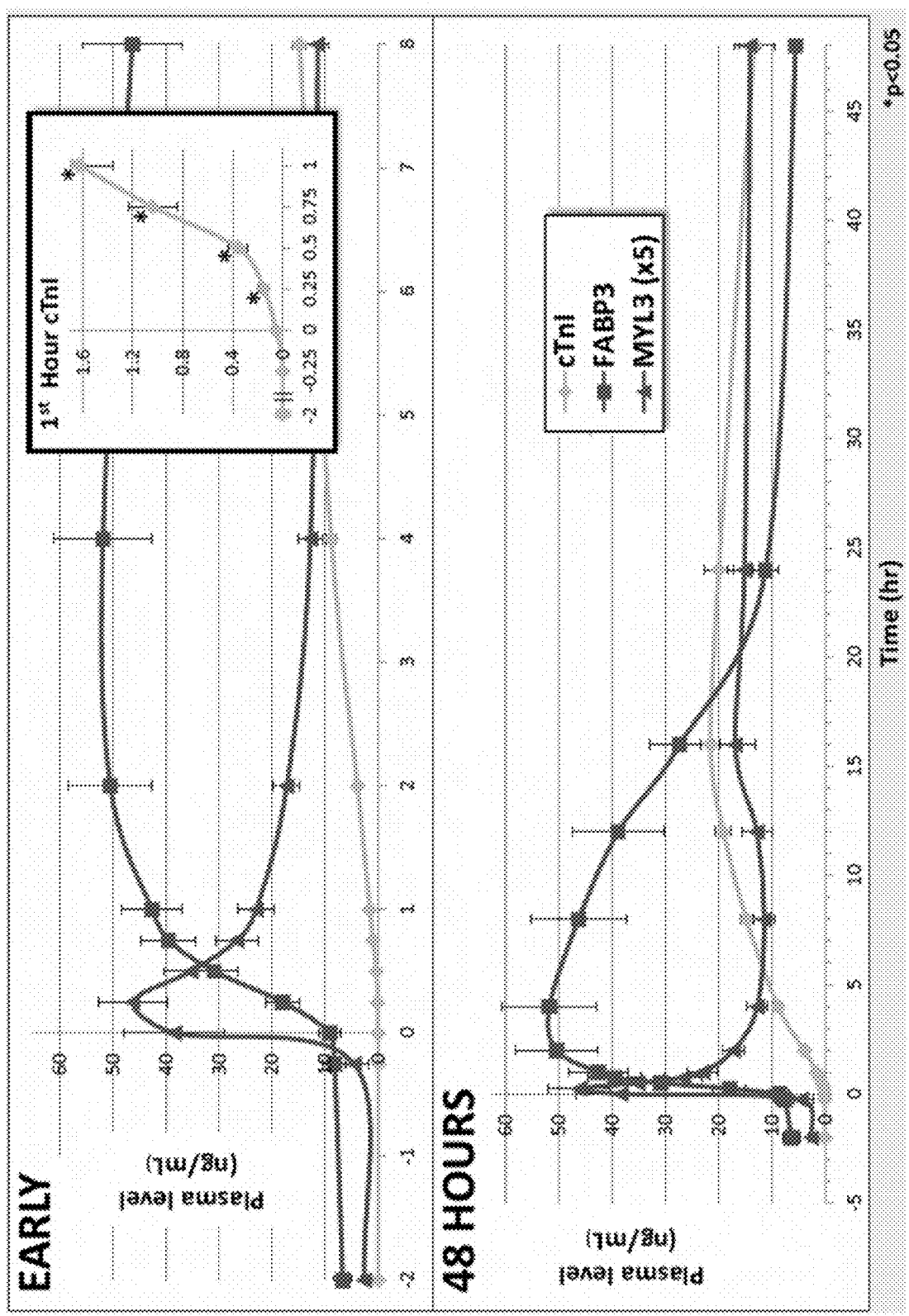
FIG. 1 depicts graphs showing time dependent changes in plasma levels of cardiac troponin I (cTnI), heart fatty acid binding protein (FABP3) and cardiac ventricular myosin alkali light chain (MYL3) following AMI (PTSMA). The top graph depicts the levels of cTnI, FABP3 and MYL3 at early timepoints (0-hours) and the bottom graph depicts the levels of cTnI, FABP3 and MYL3 at later timepoints (0-48 hours). The inset shows cTnI levels from 0-1 hours.

The present invention provides a novel molecular signature for acute cardiovascular disorders that may be detected in a biological sample of a subject. The novel molecular signature may allow earlier identification of myocardial injury and myocardial injury size, as well as the time that has elapsed since the onset of the injury. The present invention thereby allows acute myocardial injury to be ruled in, or definitively ruled out, at earlier timepoints than otherwise can be done currently with existing single biomarker assays. Further, the present invention may allow early identification of high risk groups with large evolving acute myocardial injuries at the time when they should benefit most from early aggressive interventions.

I. Molecular Signature

One aspect of the present invention provides a molecular signature to detect and/or diagnose an acute cardiovascular syndrome or disorder. In a further embodiment, the present invention provides a molecular signature to determine if a subject is at risk for an acute cardiovascular syndrome or disorder. A molecular signature is typically a protein or set of proteins, found in a biological sample, whose presence or level varies with disease state and may be readily detected. The protein or set of proteins may be found on the surface of a cell or secreted from a cell. The amount of protein may be used to establish a positive and negative threshold for that protein. The molecular signature is a specific combination of positive proteins. The detection level of the molecular signature may then be compared to a known value. The comparison may be used for several different purposes, including but not limited to, diagnosis of an acute cardiovascular syndrome or disorder, prognosis of an acute cardiovascular syndrome or disorder, and monitoring an acute cardiovascular syndrome or disorder progression and/or treatment.

As detailed in the examples, a novel combination of proteins has been identified as a molecular signature for identification of myocardial injury and/or myocardial injury size, as well as the time that has elapsed since the onset of injury. Generally, the proteins of the molecular signature are secreted from a cell. In the invention, the molecular signature comprises cardiac troponin I (cTnI), myosin light chain 3 (MYL3), and fatty acid binding protein 3 (FABP3). In a specific embodiment, the molecular signature consists of cardiac troponin I (cTnI), myosin light chain 3 (MYL3), and fatty acid binding protein 3 (FABP3). As such, an acute cardiovascular syndrome or disorder is detected or diagnosed when a biological sample is positive for cTn1, MYL3 and FABP3.

Cardiac troponin I is found in a troponin complex with two additional proteins: troponin C and troponin T. The troponin complex is integral to muscle contraction in skeletal muscle and cardiac muscle, but not smooth muscle. Cardiac troponin T (cTnT) and troponin I (cTnI) are cardiac regulatory proteins that control the calcium mediated interaction between actin and myosin. Cardiac troponins may not be detected in the serum for up to four hours after the onset of an acute coronary event. MYL3 is an alkali light chain also referred to as both the ventricular isoform and the slow skeletal muscle isoform. FABP3 may also be referred to as heart-type fatty acid binding protein (hFABP) or mammary-derived growth inhibitor. FABP3 is a small cytoplasmic protein (15 kDa) released from cardiac myocytes following an ischemic episode. FABP3 is involved in active fatty acid metabolism where it transports fatty acids from the cell membrane to mitochondria for oxidation.

The molecular signature may further comprise additional markers known to be indicative of acute cardiovascular syndrome or disorder.

II. Methods

In other aspects, the disclosure encompasses methods of detecting an acute cardiovascular syndrome or disorder in a subject. A method of the disclosure comprises: detecting a level of cardiac troponin I (cTnI), fatty acid binding protein (FABP3) and ventricular myosin alkali light chain (MYL3) in a biological sample obtained from a subject; comparing the level of cTnI, FABP3 and MYL3 detected to a reference level; and detecting an acute cardiovascular syndrome or disorder when the level of cTnI, FABP3 and MYL3 is significantly increased relative to the reference level.

In another aspect, the disclosure encompasses methods to determine the time that has elapsed since onset of an acute cardiovascular syndrome or disorder in a subject, the method comprising: detecting a level of cardiac troponin I (cTnI), fatty acid binding protein (FABP3) and ventricular myosin alkali light chain (MYL3) in a biological sample obtained from the subject at about time 0, about time 30 min and about time 60 minutes; comparing the levels of cTnI, FABP3 and MYL3 detected at about time 0, about time 30 min and about time 60 minutes; and detecting the time that has elapsed since onset of the acute cardiovascular syndrome or disorder, wherein: (i) a very early period (<1 hour) is detected by low cTnI levels, a positive rate of change and a positive change in the rate of change in cTnI, a positive rate of change and a positive change in the rate of change in FABP3, and a positive then negative rate of change and change in the rate of change in MYL3; (ii) an early period (<4 hours) is detected by a positive rate of change and a positive change in the rate of change in cTnI, a positive rate of change in FABP3, and a positive then negative change in the rate of change in FABP3; and (iii) a later period (>8 hours) is detected by high cTnI levels, a negative rate of change in cTnI and an absent rate of change and change in rate of change in FABP3 and MYL3.

In still another aspect, the disclosure encompasses a method to differentiate between a large and a small acute myocardial injury (AMI) in a subject, the method comprising: detecting a level of cardiac troponin I (cTnI), fatty acid binding protein (FABP3) and ventricular myosin alkali light chain (MYL3) in a biological sample obtained from the subject at about time 0, about time 30 min and about time 60 minutes; comparing the levels of cTnI, FABP3 and MYL3 detected at about time 0, about time 30 min and about time 60 minutes; and detecting a large AMI when the cTnI levels at 16-24 hours are greater than about 20 ng/ml and/or when the FABP3 levels are significantly elevated compared to a reference level and/or when the rate of change of cTnI and/or FABP3 are significantly elevated compared to a reference level.

(a) Subject

A biological sample may be collected from any subject at risk for an acute cardiovascular syndrome or disorder, known to suffer from acute cardiovascular syndrome or disorder, suspected of having an acute cardiovascular syndrome or disorder or used as a disease model for acute cardiovascular syndrome or disorder. As used herein, "subject" or "patient" is used interchangeably. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human.

A subject may or may not be having a symptom associated with acute cardiovascular syndrome or disorder. In some embodiments, the subject has no clinical signs or symptoms of acute cardiovascular syndrome or disorder. In other embodiments, the subject has mild clinical signs or symptoms of acute cardiovascular syndrome or disorder. In yet other embodiments, the subject may be at risk for acute cardiovascular syndrome or disorder. In different embodiments, the subject may have clinical signs or symptoms of acute cardiovascular syndrome or disorder. In still other embodiments, the subject has been diagnosed with acute cardiovascular syndrome or disorder. In different embodiments, the subject may be undergoing a procedure with a high risk of acute cardiovascular syndrome or disorder. Early diagnosis of acute cardiovascular syndrome or disorder in the subject may reduce the development and/or progression of symptoms associated with the acute cardiovascular syndrome or disorder.

As used herein, acute cardiovascular syndrome or disorder (also referred to as acute coronary syndrome) is used to describe situations where the blood supplied to the heart muscle is suddenly blocked. The blockage can be sudden and complete, or it can come and go. Non-limiting examples of an acute cardiovascular syndrome or disorder include coronary artery disease, atherosclerosis, acute myocardial injury (also referred to as acute myocardial infarction), arteriosclerosis, unstable angina pectoris, embolism, deep vein thrombosis, stroke, congestive heart failure and arrhythmia. Common signs and symptoms of an acute cardiovascular syndrome or disorder may include chest pain or discomfort, which may involve pressure, tightness or fullness; pain or discomfort in one or both arms, the jaw, neck, back or stomach; shortness of breath (dyspnea); feeling dizzy or lightheaded; nausea; sweating (diaphoresis); epigastric discomfort with or without nausea and vomiting; syncope or near syncope without other cause; and/or impairment of cognitive function without other cause.

(b) Obtaining a Sample

The presence of the molecular signature of the invention may be detected in several different biological samples. Any biological sample comprising a protein of the molecular signature is suitable. Non-limiting examples of biological samples may include whole blood, peripheral blood, plasma, serum, bone marrow, urine, lymph, bile, pleural fluid, semen, saliva, sweat, and CSF. The biological sample may be used "as is", the cellular components may be isolated from the biological sample, or a protein faction may be isolated from the biological sample using standard techniques. In one embodiment, the biological sample is selected from the group consisting of whole blood, peripheral blood, plasma, and serum. In another embodiment, the biological sample is whole blood. In yet another embodiment, the biological sample is plasma. In still yet another embodiment, the biological sample is serum.

As will be appreciated by a skilled artisan, the method of collecting a biological sample from a subject can and will vary depending upon the nature of the biological sample. Any of a variety of methods generally known in the art may be utilized to collect a biological sample from a subject. Generally speaking, the method preferably maintains the integrity of the molecular signature such that it can be accurately quantified in the biological sample. Methods for collecting blood or fractions thereof are also well known in the art. For example, see U.S. Pat. No. 5,286,262, which is hereby incorporated by reference in its entirety.

A biological sample from a subject may be obtained by freshly collecting a sample, or may be obtained from a previously collected and stored sample. For instance, a biological sample may be obtained from a collection of stored and preserved blood samples. In some embodiments, a sample is obtained by freshly collecting a sample. In other embodiments, a sample is obtained from a previously collected and stored sample.

In some embodiments, a single sample is obtained from a subject to detect the molecular signature of the invention in the sample. Alternatively, the molecular signature may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time. In a specific embodiment, three samples are collected from a subject over time.

When more than one sample is collected from a subject over time, samples may be collected every 0.25, 0.5, 1, 2, 3, 4, 5, 6, 7, 8, 9, 10, 11, 12 or more hours. In some embodiments, samples are collected every 0.25, 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days. In a specific embodiment, a sample is collected at about time 0, about 30 minutes and about 60 minutes.

(c) Detecting the Molecular Signature

A method of the disclosure comprises detecting a molecular signature of the invention in a sample from a subject. As used herein, the term "detecting a molecular signature" may be used to describe detecting the presence of the molecular signature, or detecting the presence and concentration or amount of the molecular signature in a sample from a subject. As used herein, the term "molecular signature" refers to at least cTnI, FABP3 and MYL3. It is understood that detecting the presence and concentration or amount of molecular signature is meant the detection of the presence and concentration or amount of each individual protein within the molecular signature. For example, detecting the presence and concentration or amount of cTnI, FABP3, and MYL3. In specific embodiments, a method of the disclosure comprises detecting the presence and concentration or amount cTnI, FABP3, and MYL3.

In essence, a molecular signature of the invention may be detected using methods normally used in the art for detecting a specific protein in a sample. As such, non-limiting examples of methods of detecting a protein may include chromatography, mass spectrometry, an antibody-based detection method, or a combination thereof, and may be as discussed in Ausubel et al. (2003) Current Protocols in Molecular Biology, John Wiley & Sons, New York, N.Y., or Sambrook et al. (1989) Molecular Cloning: A Laboratory Manual, Cold Spring Harbor Press, Cold Spring Harbor, N.Y.

In some embodiments, a molecular signature of the disclosure is detected using mass spectrometry. Mass spectrometry may be tandem mass spectrometry, quadrupole mass spectrometry, MALDI-TOF mass spectrometry, inductively coupled plasma-mass spectrometry (ICP-MS), accelerator mass spectrometry (AMS), thermal ionization-mass spectrometry (TIMS), and spark source mass spectrometry (SSMS). In specific embodiments, cTnI, FABP3, and MYL3 are detected using a mass spectrometry method capable of detecting a specific protein. Non-limiting examples of mass spectrometry methods capable of detecting a specific protein include MALDI-TOF mass spectrometry and high-resolution tandem mass spectrometry. In an exemplary embodiment, MALDI-TOF mass spectrometry is used to detect cTnI, FABP3, and MYL3. In another exemplary embodiment, high-resolution tandem mass spectrometry is used to detect cTnI, FABP3, and MYL3.

In other embodiments, a molecular signature of the disclosure may be detected in a sample using methods based on epitope binding agents. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion.

In some embodiments, the epitope binding agent-based method is an ELISA. In other embodiments, the epitope binding agent-based method is a radioimmunoassay. In still other embodiments, the epitope binding agent-based method is an immunoblot or Western blot. In different embodiments, the epitope binding agent-based method is immunohistochemistry (IHC). In alternative embodiments, the epitope binding agent-based method is an array. In other embodiments, the epitope binding agent-based method is flow cytometry.

In some specific alternatives of the embodiments, an epitope binding agent is an antibody, and each protein of a molecular signature of the invention may be detected using antibody based methods. Non-limiting examples of antibodies that may be used include polyclonal antibodies, ascites, Fab fragments, Fab' fragments, monoclonal antibodies, single chain antibodies, humanized antibodies, and other fragments that contain the epitope binding site of the antibody.

Antibody based methods that may be used to detect a protein of a molecular signature of the present disclosure are known in the art. Non-limiting examples of methods based on antibodies for detecting a protein may include Western blotting, enzyme-linked immunosorbent assays (ELISAs), or other solid phase immunoassays, a sandwich immunoassay, radioimmunoassay, nephelometry, electrophoresis, immunofluorescence, immunoblot, flow cytometry, immunohistochemistry, an array or other methods (see Ausubel, F. M. et al., eds., Current Protocols in Molecular Biology, John Wiley & Sons, including supplements through 2001).

In general, an antibody-based method of detecting and measuring an amount of a protein comprises contacting some or all of the sample comprising a molecular signature of the invention with an anti-cTnI, -FABP3, and/or -MYL3 antibody under conditions effective to allow for formation of a complex between the antibody and the protein. Typically, the entire sample is not needed, allowing one skilled in the art to repeatedly detect and measure the amount of a protein in the sample over time. The method may occur in solution, or the antibody or molecular signature protein may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. A molecular signature protein antibody may also be attached to the substrate non-covalently. For example, a biotinylated anti-cTnI, -FABP3, and/or -MYL3 antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-cTnI, -FABP3, and/or -MYL3 antibody composition to the sample and incubating the mixture for a period of time long enough for the anti-cTnI, -FABP3, and/or -MYL3 antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

For each of the foregoing embodiments, a protein of a molecular signature of the invention may be first isolated or enriched before detection. For instance, a protein of a molecular signature of the invention may be enriched or isolated using liquid chromatography, by precipitation, electrophoresis, or affinity purification.

(d) Detecting a Cardiovascular Syndrome or Disorder

In aspect, the invention provides means to classify a subject based on the amount of molecular signature measured in a biological sample obtained from the subject. The method generally comprises (i) measuring the amount of cTnI, FABP3, and MYL3 in a biological sample obtained from a subject, (ii) comparing the amount of cTnI, FABP3, and MYL3 in the sample to a reference value, and (iii) classifying the subject as having or at risk for a cardiovascular syndrome or disorder based on the amount of cTnI, FABP3, and MYL3 measured in the sample. In the foregoing methodology, it is understood that by "measuring the amount of cTnI, FABP3, and MYL3" is meant measuring the amount of each individual protein. Methods for obtaining a biological sample from a subject and measuring the amount of cTnI, FABP3, and MYL3 in the sample are detailed above. In a preferred embodiment, the biological sample is biological fluid selected from the group consisting of blood, plasma, and serum.

The amount of molecular signature in the sample is compared to a reference value. Any suitable reference value known in the art may be used. For example, a suitable reference value may be the amount of molecular signature in a biological sample obtained from a subject or group of subjects of the same species that has no known cardiovascular syndrome or disorder. In another example, a suitable reference value may be the amount of molecular signature in a biological sample obtained from a subject, or group of subjects, of the same species that has no detectable cardiovascular syndrome or disorder. In another example, a suitable reference value may be the amount of molecular signature in biological sample obtained from a subject or group of subjects of the same species that has a cardiovascular syndrome or disorder. For example, a suitable reference value may be the amount of molecular signature in a biological sample obtained from a subject or group of subjects of the same species that has a cardiovascular syndrome or disorder as measured by electrocardiography, blood testing, and/or echocardiography. In another example, a suitable reference value may be the background signal of the assay as determined by methods known in the art. In another example, a suitable reference value may be a measurement of the amount of molecular signature in a reference sample obtained from the same subject. The reference sample comprises the same type of biological sample as the test sample, and may or may not be obtained from the subject when cardiac function was normal. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy or progression of disease, a reference sample may be a sample obtained from a subject before therapy began. In such an example, a subject may have suspected or at risk for cardiovascular syndrome or disorder but may not have other symptoms of cardiovascular syndrome or disorder or the subject may have suspected or at risk for cardiovascular syndrome or disorder and one or more other symptom of cardiovascular syndrome or disorder. In a specific embodiment, a suitable reference value may be a threshold previously determined via other methods. For example, a suitable reference value may be a value corresponding to >0 ng/ml of cTnI, FABP3, and MYL3 as measured by immunoassay. It should be appreciated by those of skill in the art that in the foregoing embodiments, a reference value of cTnI, FABP3, and MYL3 may be determined for each protein. For example, a reference value may be established for cTnI, FABP3 and MYL3.

According to the invention, a subject may be classified based on the amount molecular signature measured in the sample. Classifying a subject based on the amount of molecular signature measured in a biological sample obtained from the subject may be used to identify subjects with a cardiovascular syndrome or disorder. The term "cardiovascular syndrome or disorder" is described in detail in Section 11(a). Generally speaking, a subject may be classified as having a high or low amount of molecular signature compared to a reference value, wherein a high amount of molecular signature is an amount above the reference value and a low amount is an amount equal to or below the reference value. In preferred embodiments, to classify a subject as having a high amount of molecular signature, the amount of molecular signature in the sample compared to the reference value may be at least 5% greater. For example, the amount of molecular signature in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of molecular signature in the sample of biological fluid obtained from the subject compared to the reference value may be increased by greater than 1-fold. For example, the amount of molecular signature in the sample compared to the reference value may be increased at least 1.5-fold, at least 2-fold, at least 2.5-fold, at least 3-fold, at least 3.5-fold, at least 4-fold, at least 4.5 fold, or at least 5-fold. Alternatively, the amount of molecular signature in the sample compared to the reference value may be increased by at least 5.5-fold, at least 6-fold, at least 6.5-fold, at least 7-fold, at least 7.5-fold, at least 8-fold, at least 8.5-fold, at least 9-fold, at least 9.5 fold, at least 10-fold, at least 15-fold, at least 20-fold, at least 25-fold, at least 30-fold, at least 35-fold, at least 40-fold, at least 45-fold, or at least 50-fold. It is understood that each individual protein in the molecular signature may have a separate value for the amount above the reference value.

In another embodiment, the increase or decrease in molecular signature is measured using p-value. For instance, when using p-value, a molecular signature is identified as being differentially expressed between a molecular signature in a biological sample and the reference value when the p-value is less than 0.1, preferably less than 0.05, more preferably less than 0.01, even more preferably less than 0.005, the most preferably less than 0.001. In a specific embodiment, acute cardiovascular syndrome or disorder is detected when the molecular signature is increased in a biological sample relative to the reference value and the p-value is less than 0.1, preferably less than 0.05, more preferably less than 0.01, even more preferably less than 0.005, the most preferably less than 0.001.

In another aspect, the invention provides means to detect a cardiovascular syndrome or disorder in a subject. In some embodiments, a cardiovascular syndrome or disorder is detected when the concentration of one or more of the proteins of the molecular signature detected in a sample from a subject is above the reference value. For instance, a cardiovascular syndrome or disorder is diagnosed when the concentration of cTnI, FABP3 and MYL3 detected in a sample is above the reference value. In another embodiment, the invention provides means to determine whether a subject is at risk for a cardiovascular syndrome or disorder.

In addition to the detection of a cardiovascular syndrome or disorder, it should also be appreciated by those of skill in the art that a method of the disclosure may be used to diagnose various features associated with a cardiovascular syndrome or disorder. A method of the disclosure may be used to determine the severity of a cardiovascular syndrome or disorder. A method of the disclosure may also be used to diagnose a cardiovascular syndrome or disorder with good prognosis that may resolve. Alternatively, a method of the disclosure may be used to a cardiovascular syndrome or disorder with bad prognosis that may lead to death.

A method of the present disclosure may be used in combination with other methods of diagnosing a cardiovascular syndrome or disorder, or other clinical diagnostic methods.

Further, the pattern of expression of a molecular signature of the invention may be used to indicate the duration of an acute cardiovascular syndrome or disorder. Accordingly, by evaluating the molecular signature over time, it may be determined the amount of time that has elapsed since onset of the cardiovascular event. In another embodiment, the pattern of a molecular signature of the invention may be used to differentiate between a large and a small acute myocardial injury in a subject. In still another embodiment, comparison of the molecular signature obtained from the subject to a known profile of molecular signature may indicate the duration of an acute cardiovascular syndrome or disorder. As used here, a "profile of molecular signature" may be used to describe the identity and/or the concentration of each protein of the molecular signature over time during a cardiovascular syndrome or disorder. The profile of molecular signature may be obtained from a database comprising the identity and concentration of each protein in the molecular signature correlated with the duration of a cardiovascular syndrome or disorder. The duration of an acute cardiovascular syndrome or disorder may be identified by matching and entry of the database to the presence and concentration of each protein in the molecular signature in the sample, thereby determining the duration of an acute cardiovascular syndrome or disorder. In some embodiments, a profile of molecular signature may comprise cTnI, FABP3, and MYL3. In some embodiments, a profile of molecular signature may consist of cTnI, FABP3, and MYL3. For example, high levels of MYL3 in combination with the presence of cTnI and FABP3 may indicate early on in the onset of an acute cardiovascular syndrome or disorder (i.e. <2 hours). Alternatively, high levels of FABP3 in combination with the presence of cTnI and MYL3 may indicate slightly later on in the onset of an acute cardiovascular syndrome or disorder (i.e. 2-4 hours). Further, similar levels of cTnI, FABP3 and MYL3 may indicate later on in the onset of an acute cardiovascular syndrome or disorder (i.e. 16-24 hours). See, for example, FIG. 1. As used herein, high levels may mean greater than about 30 ng/ml. Specifically, high levels may mean greater than about 30, about 35, about 40, about 45, about 50, about 55, or about 60 ng/ml.

Figure 2A:
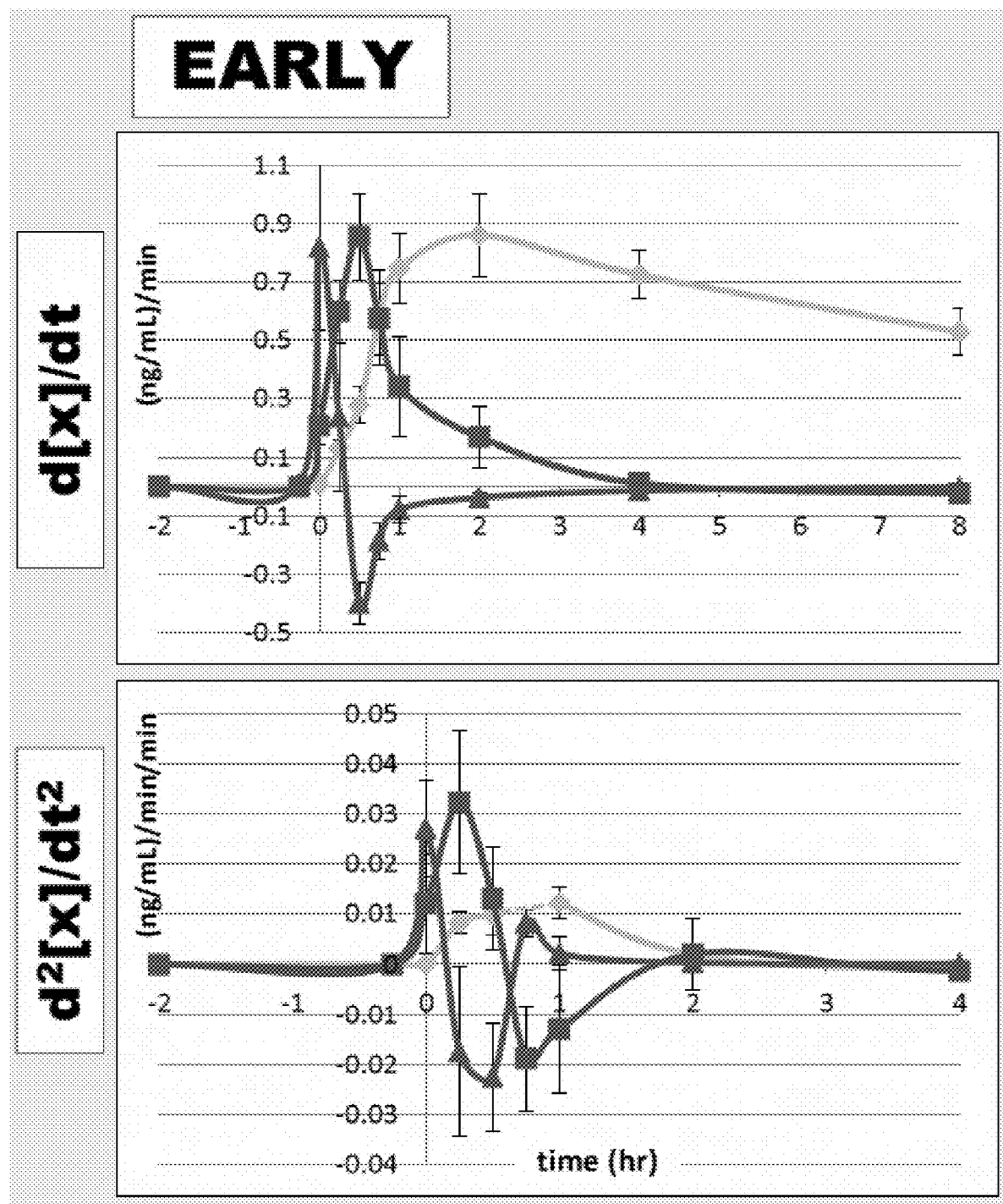
FIG. 2A and FIG. 2B depict cTnI, FABP3 and MYL3 changes as a function of time ($d[x]/dt$ and $d^2[x]/dt^2$) following PTSMA.
Figure 2B:
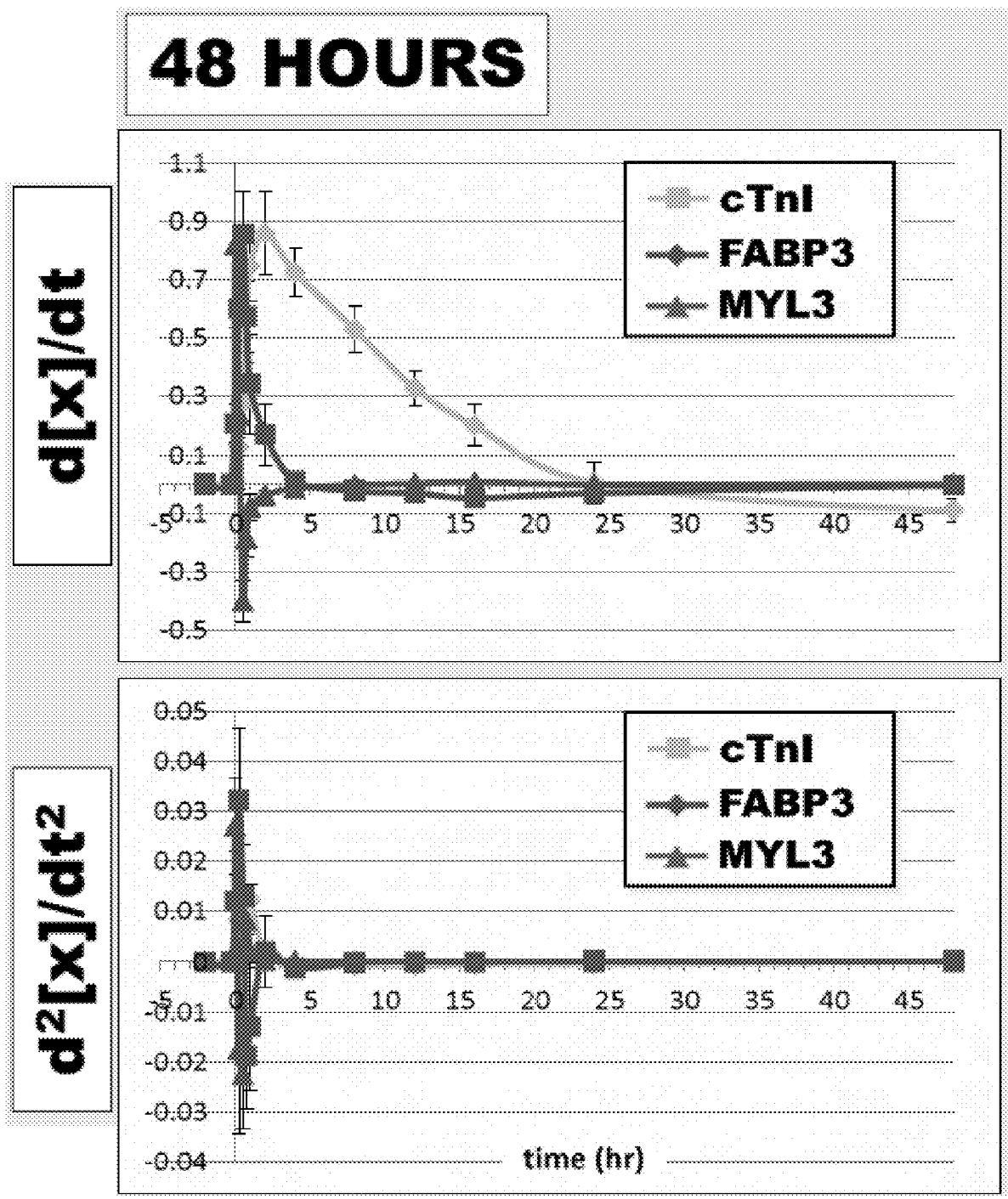

Additionally, the rate of change of the molecular signature and the change in the rate of change may be used to determine the time that has elapsed since the onset of an acute cardiovascular syndrome or disorder. For example, a very early period (<1 hour) may be detected by low cTnI levels, a positive rate of change and a positive change in the rate of change in cTnI, a positive rate of change and a positive change in the rate of change in FABP3, and a positive then negative rate of change and change in the rate of change in MYL3 (see, for example, FIG. 2A). Additionally, an early period (<4 hours) may be detected by a positive rate of change and a positive change in the rate of change in cTnI, a positive rate of change in FABP3, and a positive then negative change in the rate of change in FABP3 (see, for example, FIG. 2A). Further, a later period (>8 hours) is detected by high cTnI levels, a negative rate of change in cTnI and an absent rate of change and change in rate of change in FABP3 and MYL3 (see, for example, FIG. 2B).

Upon detection or diagnosis of a cardiovascular syndrome or disorder, the subject may be treated via methods standard in the art for a cardiovascular syndrome or disorder. Such treatment methods may depend on the severity of the cardiovascular syndrome or disorder. Treatment for a cardiovascular syndrome or disorder consists primarily of expedient restoration of normal coronary blood flow and the maximum salvage of functional myocardium. The subject may be administered antiplatelet agents such as aspirin or clopidogrel, supplemental oxygen, nitrates, pain medication, beta blockers such as metoprolol, atenolol or carvedilol, unfractionated heparin, low-molecular-weight heparain such as dalteparin or enoxaparin, warfarin, fibrinolytics, angiotensin-converting enzyme inhibitors and angiotensin receptor blockers such as captopril, Ramipril, captopril or Lisinopril, glycoprotein IIb/IIIa antagonists such as abciximab, eptifibatide, or tirofiban, statin therapy, or aldosterone antagonists. More aggressive treatment options may include percutaneous coronary intervention, surgical revascularization or implantable cardiac defibrillators.

For each aspect, the method generally comprises (i) obtaining a biological sample from a subject, (ii) measuring the amount of molecular signature in the sample, and (iii) comparing the amount of molecular signature in the sample to a reference value. A greater amount of molecular signature in the sample compared to the reference value indicates a cardiovascular syndrome or disorder. The amount of molecular signature may be a qualitative, a semi-quantitative or quantitative measurement. Suitable molecular signatures are described above, as are methods for measuring the amount of molecular signature in a biological sample. In a preferred embodiment, the biological sample is selected from the group consisting of blood, plasma, and serum.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Early Biomarkers of Myocardial Injury

Introduction:

Detection of acute myocardial injury (AMI) remains challenging, particularly as it relates to identification of patients with significant evolving AMI events that could benefit most from early use of invasive approaches. Cardiac specific biomarkers have the potential to help distinguish high risk groups, although the cardiac troponins now widely used to specifically identify AMI events typically rise slowly following AMI, and very small elevations which are now detectable early with high sensitivity assays can be nonspecific and difficult to interpret. In this study we examined cardiac biomarker profiles in patients with severe hypertrophic cardiomyopathy (HCM) undergoing percutaneous septal myocardial ablation (PTSMA) in the cardiac catheterization lab. This procedure provides a human model of AMI with a defined time of occurrence.

Methods:

Plasma samples were obtained from patients at frequent intervals immediately preceding and following the PTSMA procedure. Cardiac troponin I (cTnI) levels were measured using the clinical chemistry laboratory Siemens Dimensions RxL assay system. Early cTnI level increases were measured with a high sensitivity cTnI assay using the Singulex Erenna immunoassay system. Mass spectrometry was used to identify putative early protein biomarkers of AMI, and immunoassays were then developed for high throughput analysis of plasma samples. Heart fatty acid binding protein (FABP3) was measured using an R&D FABP3 ELISA assay kit. Ventricular myosin alkaline light chain (MYL3) was measured with a sandwich ELISA using a mouse anti-MYL3 monoclonal antibody and a goat anti-MYL3 polyclonal antibody (detection). Peak [cTnI] was used to categorize 'large' (≥20 ng/ml, n=5) vs 'small' (<20 ng/ml, n=13) MI (PTSMA) events.

Results:

Cardiac troponin I (cTnI), heart fatty acid binding protein (FABP3), and ventricular myosin alkali light chain (MYL3), display markedly different time-dependent changes in plasma levels following AMI (PTSMA). Comparing the three markers, cTnI rises slowly and peaks late (16-24 h), while FABP3 rises more rapidly and peaks much earlier (2-4 h), and MYL3 peaks very early (<1 h) and declines very rapidly in 4 hours (FIG. 1).

The first 2 hrs are characterized by dynamic changes in $d[x]/dt$ and $d^2[x]/dt^2$ for the 3 biomarkers (FIG. 2). $d[FABP3]/dt$ remains positive for 2 hours, while $d[cTnI]/dt$ (cTnI $\Delta$) remains positive for 16 hours post-PTSMA. An early period (<4 h) is defined by positive (+) first derivative ($\Delta$) and second derivatives ($\Delta\Delta$) for cTnI, as well as +$\Delta$, and + then negative (−) $\Delta\Delta$ for FABP3. A very early period (<1 h) is defined by low cTnI levels (FIG. 1) but +$\Delta$ cTnI and $\Delta\Delta$ cTnI, as well as +FABP3 $\Delta$ and $\Delta\Delta$, and + then −MYL3 $\Delta$ and $\Delta\Delta$. A later period (>8 hr) is defined by high cTnI levels, but (−) cTnI $\Delta$ and absent FABP3 and MYL3 $\Delta$ and $\Delta\Delta$.

Figure 4A:
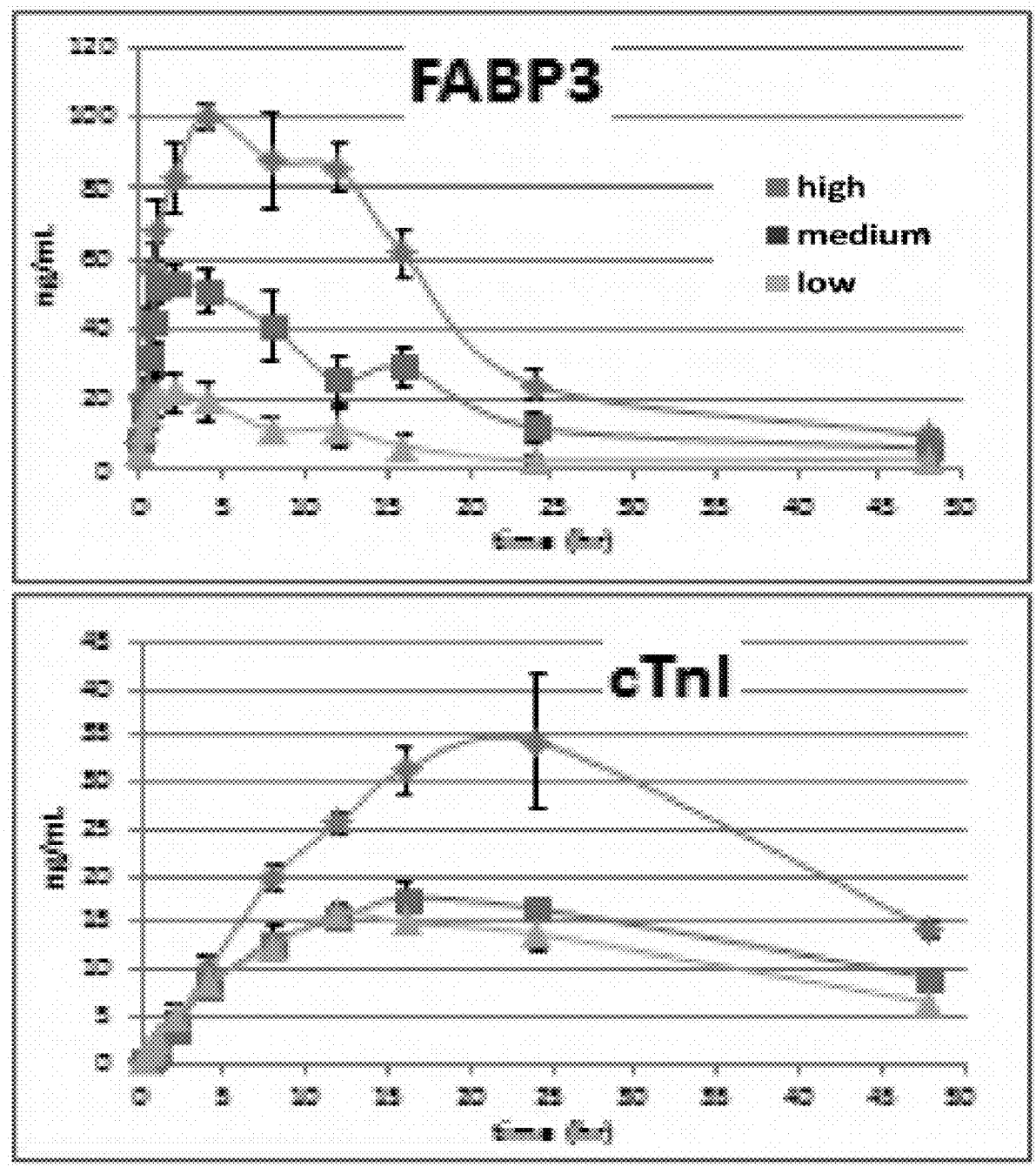
FIG. 4A and FIG. 4B depict graphs showing that (FIG. 4A) FABP3 and cTnI levels following AMI (PTSMA), and areas under the curves (AUC) for (FIG. 4B) FABP3 and cTnI in 15 subjects separated into "high", "medium" and "low" groups based on FABP3 peak levels (n=5 per group). Note that "high" FABP3 (at 2-4 h) predicts higher peak cTnI (at 16-24 h) and larger cTnI AUC.
Figure 4B:
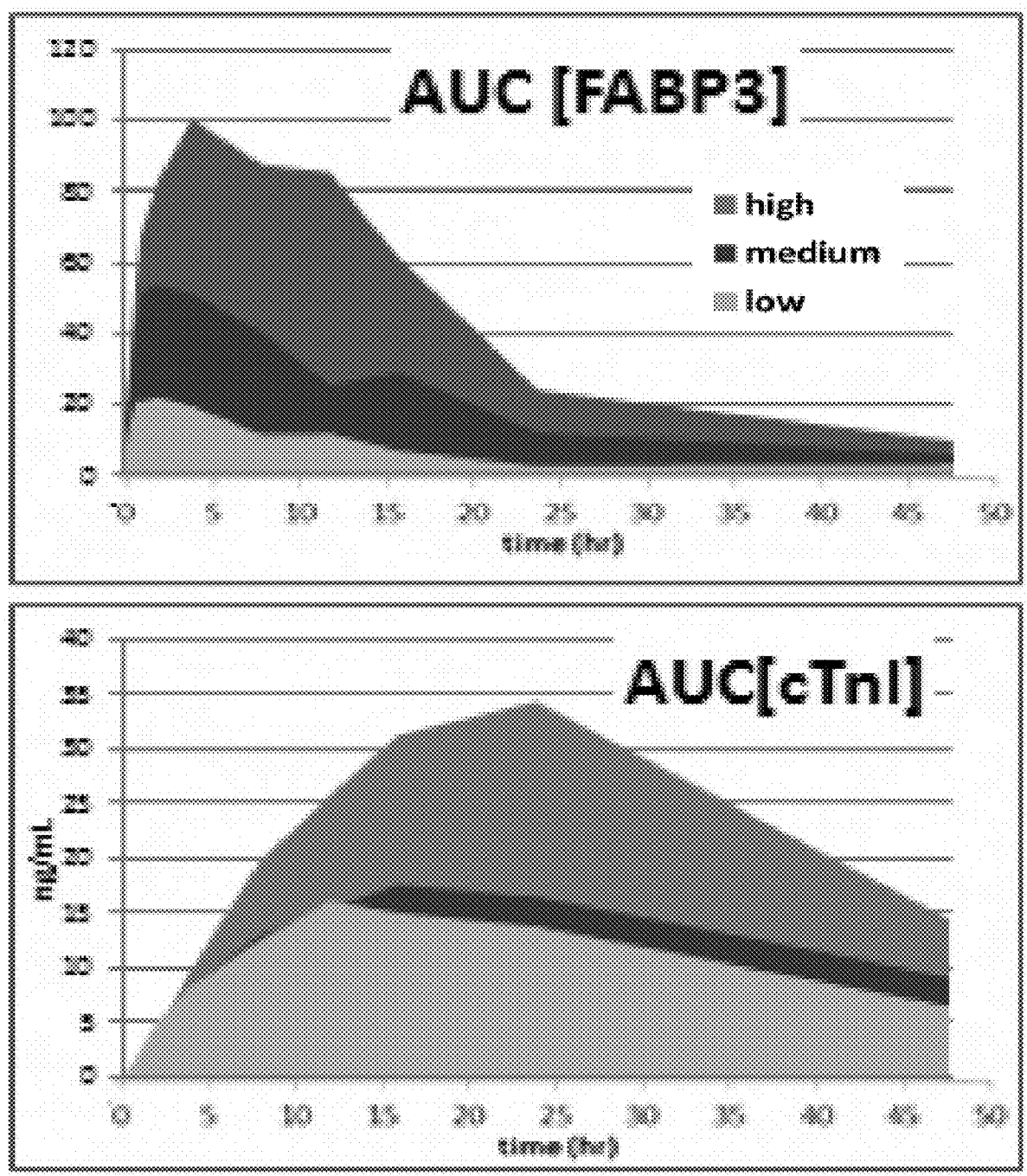

As shown in FIG. 4, the early (2-4 h) FABP3 peak can predict the peak in cTnI, and the cTnI AUC. High FABP3 levels (>50 ng/ml) and larger FABP3 areas-under-curve (AUCs) predict higher peak cTnI and cTnI AUCs. The high FABP3 group is evident by 2 hr compared to the high TnI group at 10 hr, with peak FABP3 at 4-6 hr and peak cTnI at 16-24 hr.

Figure 3:
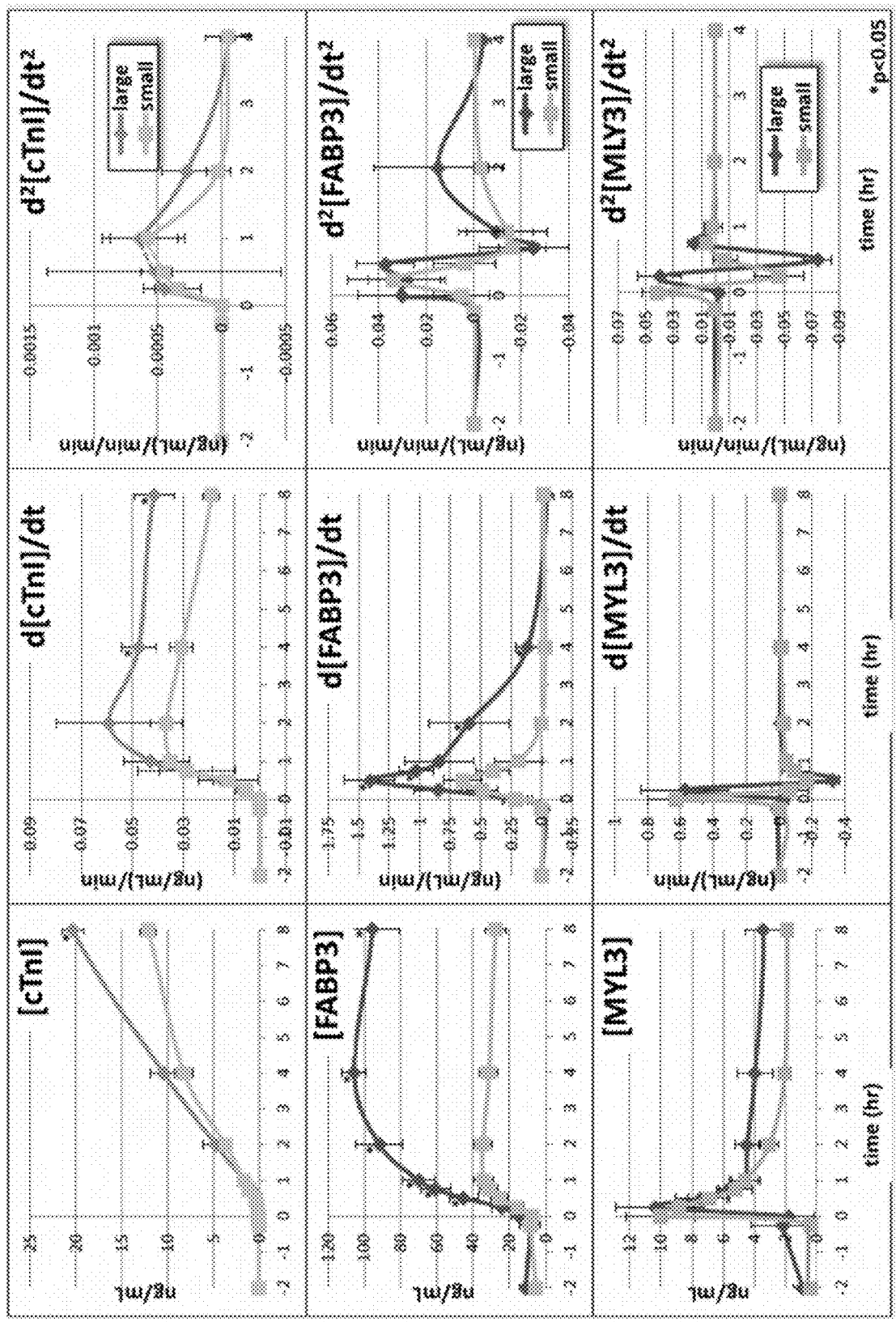
FIG. 3 depicts the comparison of 'large' (n=5) and 'small' (n=13) MI events (PTSMA) at early time points.

Early differences in [FABP3] and d[FABP3]/dt are found between 'large' from 'small' MI events (PTSMA), while differences in [cTnI] and d[cTnI]/dt are not evident until much later (FIG. 3). Larger and smaller AMI events (PTSMA) can be distinguished based on peak cTnI levels at 16-24 hr [smaller=peak cTnI<20 ng/ml; larger=peak cTnI>20 ng/ml]. Larger and smaller AMI events can be distinguished at earlier time points from FABP3 levels (FIG. 4) as well as from $\Delta$ cTnI and $\Delta$ FABP3. MLY3 increases are evident very early but peak levels and $\Delta$ values do not distinguish large from small events. $\Delta\Delta$ values are only evident very early, and do not distinguish large from small events.

Summary:

The three cardiac biomarkers we characterized have markedly different time profiles following an AMI event (PTSMA). MYL3 rises immediately and falls rapidly over a few hours. FABP3 rises rapidly over 2-4 hrs then declines to baseline over 24 hrs. cTnI rises over 16-24 hrs and then slowly declines over 72 hr toward baseline.

Quantification of the rate of change in levels of the three biomarkers ($\Delta$'s), as well as changes in the rate of change ($2^{nd}$ derivative, $\Delta\Delta$'s) provide information about the time that has elapsed since the AMI event. Very early MYL3 levels cannot predict larger from smaller events, but FABP3 levels can distinguish larger from smaller events as early as 1-2 hr. cTnI $\Delta$ and $\Delta\Delta$, and FABP3 $\Delta$ also distinguish larger from smaller events at early time points.

Conclusions:

These data demonstrate significantly different time courses for changes in plasma levels of the three cardiac biomarkers studied following an AMI event. While measurement of cTnI will remain important with respect to cardiac specificity (both MYL3 and FABP3 are also expressed in skeletal muscle), and sustained cTnI elevations provide a reliable indicator of a cardiac event, MYL3 and FABP3 appear to provide considerable additional information to help distinguish AMI at early time-points, and allow improved ability to interpret early low level elevations of cTnI. MYL3 appears to be a very early biomarker of myocardial injury. This very early signal may represent release of a cytoplasmic pool of the small MYL protein (20 kDa) from injured cells. FABP3 appear to provide considerable additional information to help distinguish AMI at early time points, and may allow improved ability to interpret early low-level elevations of cTnI. FABP3 levels may be useful to distinguish higher risk subjects with larger AMI events at early time points—when they may benefit most from early aggressive intervention.

Additionally, used in combination, these early biomarkers provide an opportunity to both clarify the time that has elapsed since the onset of the AMI event, and to potentially distinguish higher risk groups with larger evolving AMI events, who may benefit most from early aggressive intervention.

Figure 6:
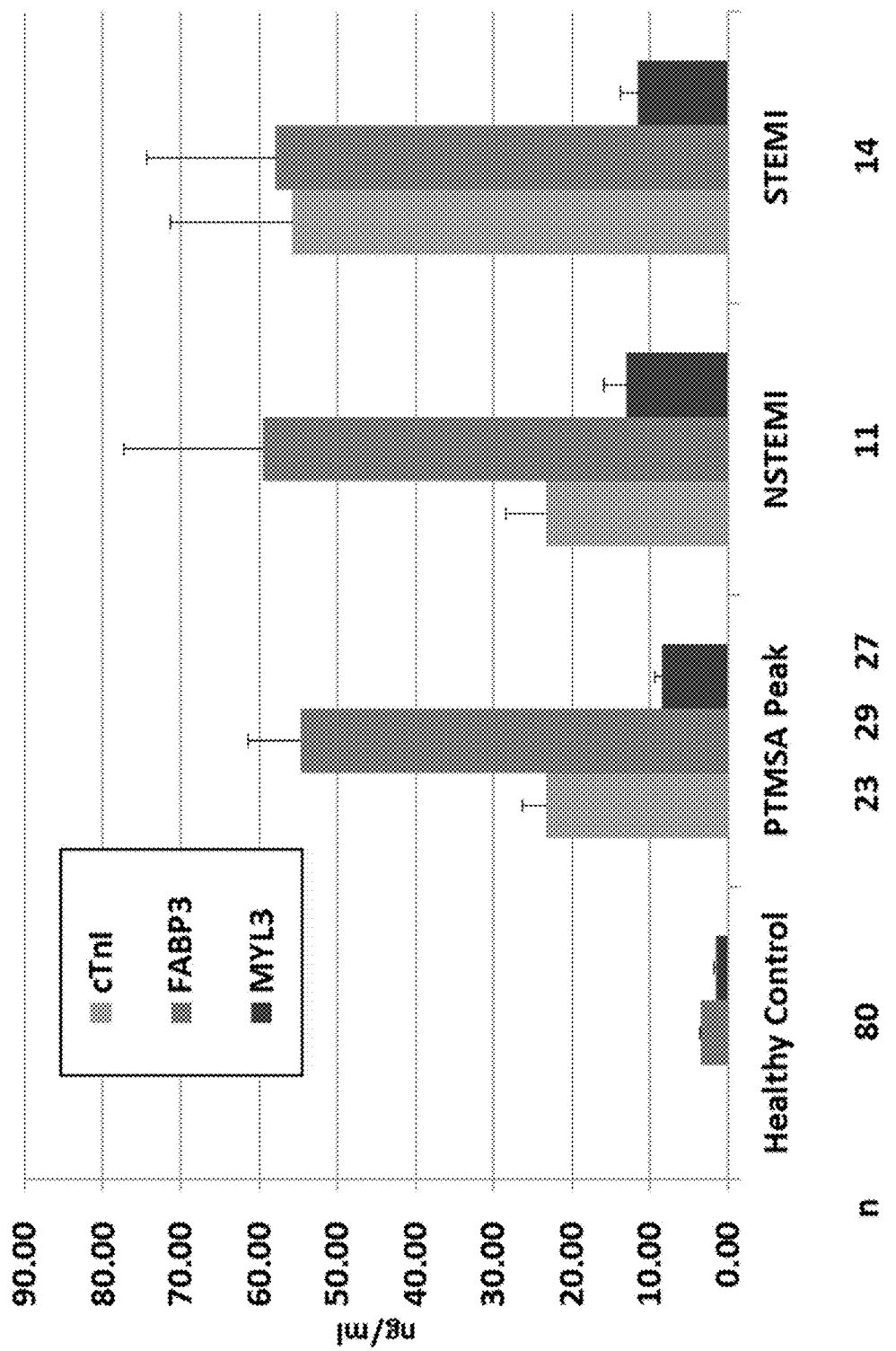
FIG. 6 depicts a graph showing the average cTnI, MYL3, and FABP3 values for healthy control, PTMSA patients and NSTEMI and STEMI AMI controls. The levels for the PTMSA peak is cTnI=16 hrs, MYL3=0.25 hrs, and FABP3=4 hrs. cTnI values from contemporary assay. No cTnI values were obtained for the healthy controls. (Error bars=SEM)

Example 2. Cardiac Risk Index and Stratification Profile' ('CRISP') for Early Diagnosis of Ischemic MI In the PTSMA model of MI with a defined time of occurrence, we demonstrated that (1) cardiac troponin I (cTnI) changes from baseline measured with a high sensitivity (hs) cTnI assay exceed recently defined 'cTnI delta' diagnostic threshold values (i.e., absolute changes in pg/mL/min) at the earliest measured time point (15 min) following PTSMA; (2) large changes in heart fatty acid binding protein (FABP3) levels ('FABP3 delta') are also evident at 15 min; and (3) large changes in ventricular myosin light chain (MYL3) occur immediately and decline rapidly over a few hours (Example 1). We hypothesize that the early changes in cTnI, FABP3 and MYL3 following ischemic MI will closely mirror those we have observed following PTSMA. We have shown that all three biomarkers are increased in patients with both STEMI and non-STEMI MI (FIG. 6). This data is comparable to the peaks seen in the PTSMA group. We will utilize the early levels and changes in levels of these three biomarkers (cTnI, FABP3 and MYL3) to iterate a novel 'cardiac risk index and stratification profile' ('CRISP') for early diagnosis of ischemic MI.

Figure 5A:
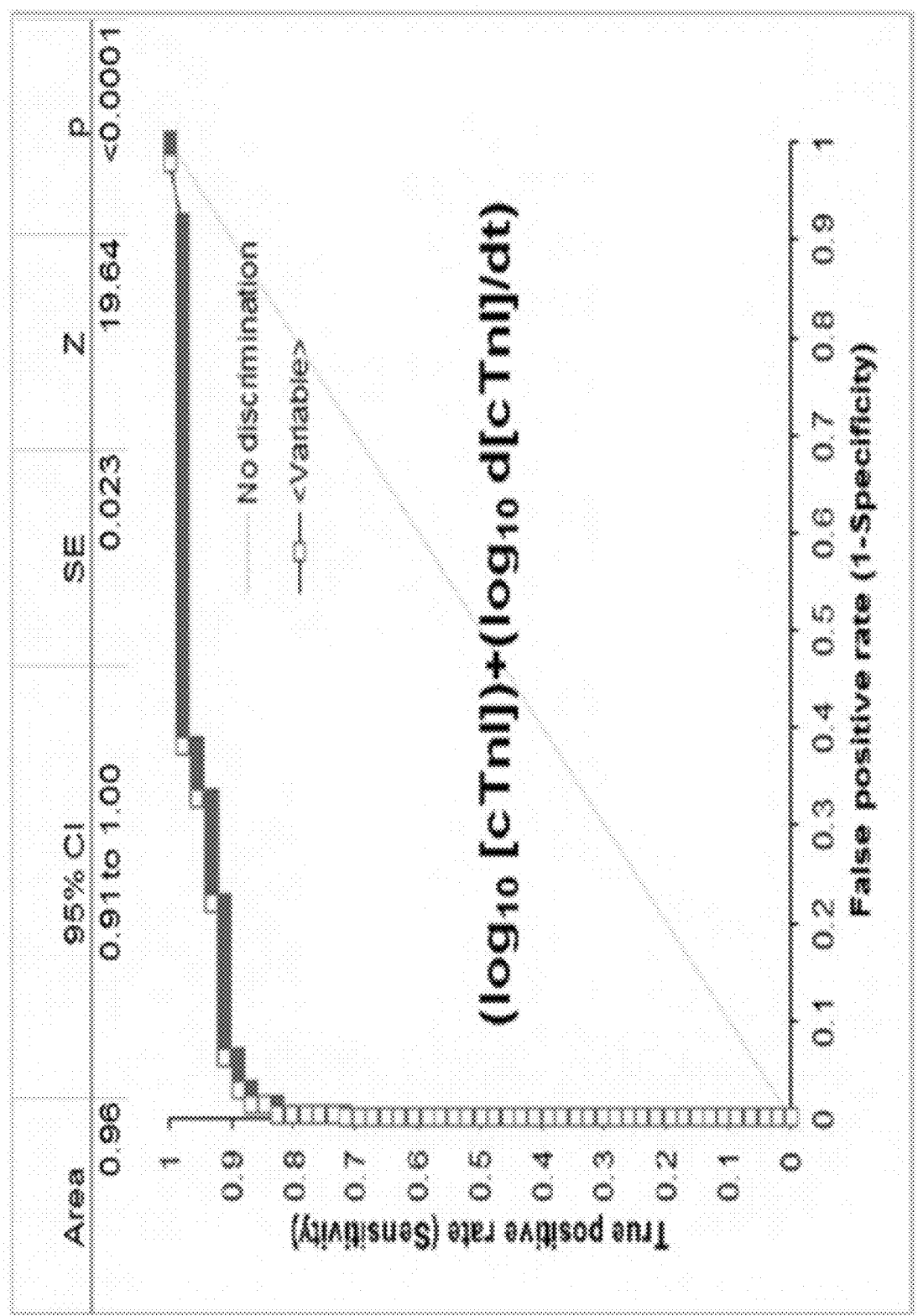
FIG. 5A and FIG. 5B depict results from two iterations of CRISP (Cardiac Risk Index and Stratification Profile). The ROC characteristics for the CRISP(s) shown in FIG. 5A and FIG. 5B represent the sum of these two parameters (initial cTnI level and $d[cTnI]/dt$) calculated as $[\log_{10}$ initial hs cTnI (in pg/ml)$]+[\log_{10} d[cTnI]/dt$ (in fg/mL/hr)$]$ (FIG. 5A) and $[\log_{10}$ of initial cTnI (in pg/ml)$]+[\log_{10}$ absolute value of $d[cTnI]/dt$ ($|d[cTnI]/dt|$) (in fg/mL/hr]$ (FIG. 5B).
Figure 5B:
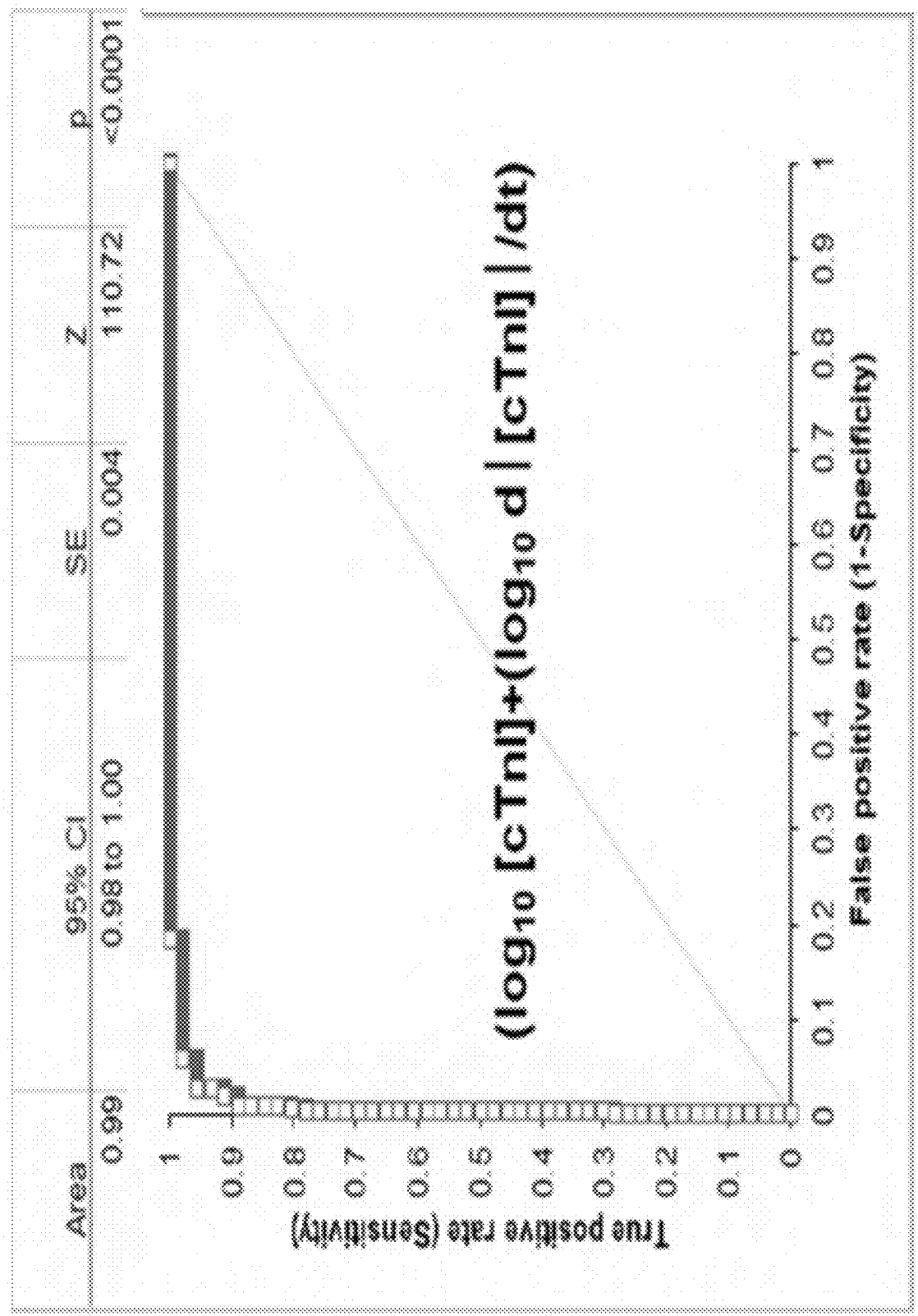

A validation trial of a hs cTnI assay was done in patients presenting to the BJH ED with chest pain, or other signs or symptoms suggestive of possible MI. In total, 601 patients had an initial plasma cTnI concentration measured with the hs assay at presentation and a second concentration measurement with this assay 6 to 24 hr after the first. These patients were subsequently adjudicated as +MI and −MI by two cardiology experts, with 46 of the 601 patients ultimately adjudicated as +MI. Note that we used this adjudication data to estimate that 1000 patients in the present proposal would yield 70-80+MI patients, and we used the measured cTnI levels at the two time points to explore the use of combinations of cTnI plasma levels ([cTnI]) and changes (d[cTnI]/dt) in the development of CRISP. The ROC characteristics for the initial hs cTnI value alone while having reasonable ROC characteristics (AUC 0.93) it appeared to have little diagnostic value based on a specificity of 20% at 98% sensitivity and a positive predictive value (PPV) of only 9% (not shown). However, a combination of initial cTnI concentration with calculated changes in cTnI (d[cTnI]/dt) (i.e., between the initial and the second cTnI sample measurements) yielded a series of iterations and the tentative CRISP with improved sensitivity and specificity for MI, with the final 2 iterations shown in FIG. 5. For these CRISP iterations, we explored various scaling and normalization methods for the two parameters, ultimately finding that scaling CRISP using $\log_{10}$ transformations for levels and changes, and normalization of changes (d[cTnI]/dt) to fg/mL/60 min provided the most useful diagnostic information. The ROC characteristics for the CRISP(s) shown in FIG. 5A and FIG. 5B represent the sum of these two parameters (initial cTnI level and d[cTnI]/dt) calculated as [$\log_{10}$ initial hs cTnI (in pg/ml)]+[$\log_{10}$d [cTnI]/dt (in fg/mL/hr)] (FIG. 5A) and [$\log_{10}$ of initial cTnI (in pg/ml)]+[$\log_{10}$ absolute value of d[cTnI]/dt (ld[cTnI]/dtl) (in fg/mL/hr] (FIG. 5B). The improved ROC characteristics with this latter iteration (using absolute values for d[cTnI]/dt in FIG. 5B) was related to a small group of +MI patients that had initially elevated cTnI levels that declined between the first and second cTnI measurement but were adjudicated as +MI. Accordingly, the negative [cTnI]/dt values in these +MI patients with declining cTnI levels resulted in a larger number of false positives at the lower cutoff value required to minimize false negatives (FIG. 5A) and that was improved to nearly perfect ROC characteristics by using absolute values for d[cTnI]/dt in the final iteration (FIG. 5B). In this final iteration, at a cutoff value equal to the lowest CRISP value (3.0) in the +MI group [i.e., no false negatives; sensitivity and negative predictive value (NPV)= 100%] the specificity was 82% with a positive predictive value (PPV) of 31%. A slightly higher cutoff CRISP threshold value (4.0) using the same CRISP formula yielded a sensitivity of 97.8% (1 false negative; NPV of 99.8%), and a specificity of 94.1%, and PPV of 57.7%. In either case, it was clear that even at the more conservative cutoff with 100% sensitivity and NPV, 458 of the 601 patients (76%) could have been adjudicated as −MI based on the tentative CRISP with 100% certainty. Certainly reliable predictive information such as this at early time points could lead caregivers to potentially release many of patients from evaluation or safely discharge them from the hospital. Notably in the cohort of 601 patients included in this evaluation, only 143 were discharged from the ED. The remaining 458 were admitted to the hospital for observation.

To further analyze more complex combinations of parameters, a multifactor logistic regression model will be developed. This approach will permit the assessment of the variables which are significantly and independently associated with +MI, and therefore which parameters may contribute to development of an optimal CRISP from the biomarker data obtained. For these analyses potential CRISP variables will include (i) individual plasma concentrations ([x]) for each biomarker ([cTnI], [FABP3] and [MYL3]) at each of the measured time points (0, 30 min and 60 min), (ii) the individual time-dependent concentration changes (d[x]/ dt) for each biomarker (including changes between time 0 and 30 min, time 0 and 60 min, and 30 and 60 min), and (iii) changes in d[x]/dt values (i.e., $2^{nd}$ derivative, $d^2[x]/dt^2$, 'acceleration') over the 60 min trial. Variables which contribute to MI diagnosis will be incorporated into an optimal CRISP, informed by correlation coefficients in the logistic regression model, with iterations of an optimal CRISP using scaling and normalization techniques as done in the development of the CRISP as described above. The optimal CRISP will provide optimal accuracy as determined by ROC AUC, with the added requirement for threshold values with a high sensitivity for MI (>98%), and a high NPV (>99.5%) for values below the threshold. Good specificity (>90%) and positive predictive value (>50%) should match or improve on that obtained with the CRISP described above.

Methods for Example 2.

Patient Identification and Sample Collection Methodology:

Patients being evaluated for MI will be identified via the Computer-Assisted Subject Enrollment in the Emergency Department (CASE-ED) screening program. CASE-ED will be programmed to screen the electronic medical record every 15 min for identified criteria, and will then send an automated message to the research team of a potential study patient in the BJH ED. For this study, CASE-ED will be programmed to report patients who have an order for a troponin and any of the following chief complaints: chest pain, heart beat—rapid or irregular, painful chest—non-traumatic, palpitations, or syncope. Patients identified by CASE-ED will then be immediately screened for inclusion in the study with inclusion criteria of (1) Patient presenting to emergency department with symptoms suggestive of possible acute coronary syndrome; (2) Patient receiving an electrocardiogram (EKG) and initial clinical cTnI level sent for testing to evaluate for possible acute coronary syndrome; and (3) Intravenous line (IV) successfully placed. Exclusion criteria include (1) Non-English speaking; (2) Unable to provide informed consent; (3) Less than 18 years of age; (4) unable to obtain or refusal of IV line placement. Potential subjects will then be immediately approached (within 15 min) for inclusion and consented by dedicated research coordinators within the Washington University Emergency Care Research Core. These coordinators are available 7 am-11 pm everyday including weekends. For patients who qualify and provide informed consent, consent will include permissions to obtain 3 additional blood samples from the IV at 0, 30 and 60 minutes from the time of enrollment. Samples from the IV will be collected by research nursing personnel familiar with this technique to ensure that contamination from IV fluid does not occur. Samples will be labeled per protocol with an assigned study number without identifiers, processed, and stored for subsequent batch analysis of hs cTnI, FABP3, and MYL3. De-identified samples will be linked to a clinical data that will include the 24 hr clock times the three samples were collected, patient demographics, chest pain symptomatology, time since onset of symptoms, presenting electrocardiogram, co-morbid conditions, length of stay, discharge diagnosis, risk stratification (TIMI score), and disposition. All de-identified clinical and sample analysis data will be stored using a Research Electronic Data Capture (REDCap) database. Linkages via medical record number will be kept in a secure and locked area that is only accessible to administrative personnel. Subjects will be followed for 30 days after enrollment to assess for any major adverse cardiac events. To reduce bias, research staff responsible for performing the cTnI, FABP3, and MYL3 assays will receive de-identified samples and will be blinded to all aspects of subject clinical data including history, clinical laboratory cTnI values, diagnoses and outcomes. Research staff responsible for clinical data collection and MI adjudication will likewise be blinded to cTnI, FABP3, and MYL3 assay results from the research labs.

Adjudication of +MI and −MI Groups:

For subjects enrolled in the protocol, the presence of major adverse cardiovascular events, including death due to cardiovascular causes, myocardial infarction, and unstable angina requiring urgent coronary revascularization, will be adjudicated by two cardiologists coordinated by co-investigator RGB. Clinical data will be reviewed for all patients, and relevant cardiac events will be ascertained from medical records, EKGs, laboratory data, stress test results, myocardial imaging, cardiac catheterization results, and 30 day follow-up. Events will be adjudicated on the basis of application of standardized endpoint definitions consistent with the 2014 ACC/AHA Key Data Elements and Definitions for Cardiovascular Endpoint Events in Clinical Trials.[7] For the purpose of this study, inclusion in the myocardial infarction group (+MI) will require evidence of myocardial necrosis in a clinical setting consistent with myocardial ischemia. This inclusion (+MI) will require the combination of: (1) evidence of myocardial necrosis (either changes in cardiac biomarkers above the diagnostic threshold or post-mortem pathological findings); and (2) supporting information derived from the clinical presentation, EKG, or the results of myocardial or coronary artery imaging. The clinical, EKG, and cardiac biomarker information will be considered to determine whether or not a MI has occurred. Specifically, timing and trends in cardiac biomarkers and EKG information will be carefully analyzed. The adjudication of +MI will also take into account the clinical setting in which the event occurs. The clinical presentation should be consistent with a diagnosis of myocardial ischemia and infarction. Cardiac biomarkers (troponins preferred) will be interpreted in relation to the upper reference limit (URL). For potential later subgroup analysis, all +MI events will be categorized by MI subtype as outlined in the Third Universal Definition for Myocardial Infarction.[8] This definition includes EKG changes supporting or confirming an MI including: ST elevation (new ST elevation at the J point in two contiguous leads with the cut-points: ≥0.1 mV in all leads other than leads V2-V3 where the following cut-points apply: ≥0.2 mV in men≥40 years (≥0.25 mV in men<40 years; or ≥0.15 mV in women); or ST depression or T-wave changes (new horizontal or down-sloping ST depression 0.05 mV in two contiguous leads and/or new T inversion ≥0.1 mV in two contiguous leads with prominent R wave or R/S ratio >1). Supporting evidence may be ischemic changes and confirmatory information may be new pathologic Q waves. When the EKG changes meet the criteria for MI diagnosis, the +MI group will be subtyped as follows: Type 1, spontaneous MI related to ischemia due to a primary coronary event such as plaque fissuring or rupturing; Type 2, MI secondary to ischemia due to imbalance between oxygen demand and supplies, e.g., coronary spasm; Type 3 MI (sudden cardiac death occurring before blood samples could be obtained); Type 4a MI (associated with PCI), Type 4b MI (associated with stent thrombosis documented by angiography or autopsy); and Type 5 MI (associated with CABG). Although not expected to contribute substantially to patients being evaluated for MI in the ED, any patient identified by the adjudicators as Type 3, 4a, 4b, and 5 MI will be excluded from consideration. Patients with unstable angina will also be excluded, including patients with ischemic discomfort (angina, or symptoms thought to be equivalent) 10 minutes in duration occurring at rest, or in an accelerating pattern with frequent episodes associated with progressively decreased exercise capacity, AND prompting an unscheduled hospitalization within 24 hours of the most recent symptoms, defined as an admission to an inpatient unit or a visit to an emergency department for at least a 24 hour stay, AND at least one of the following: (1) new or worsening ST or T wave changes on resting ECG (in the absence of confounders, such as LBBB or LVH); (2) definite evidence of inducible myocardial ischemia as demonstrated by a positive exercise stress test, and believed to be responsible for the myocardial ischemic symptoms/signs; (3) angiographic evidence of new or worse 70% lesion and/or thrombus in an coronary artery that is believed to be responsible for the myocardial ischemic symptoms/signs; (4) need for coronary revascularization procedure (PCI or CABG) for the presumed culprit lesion(s). This criterion would also be fulfilled if revascularization was undertaken during the unscheduled hospitalization; AND (5) negative cardiac biomarkers and no evidence of MI.

Measurement of Plasma Levels of cTnI, FABP3 and MYL3 at the Three Time Points in +MI and −MI Patients:

+MI patients identified and a cohort of 225 control −MI patients (3× estimated +MI cohort) matched based on co-morbid conditions and thrombolysis in myocardial infarction (TIMI) scores will have plasma samples analyzed for cTnI, FABP3 and MYL3. All samples will be run in duplicate. A group of high and low sample standards from prior studies will be included in each assay to assess for interassay variability.

High Sensitivity cTnI Assay:

cTnI concentrations in EDTA plasma will be determined using the Abbott Architect i2000 chemiluminescent microparticle immunoassay method according to the manufacturer's instructions for use. The lower limit of quantification for the hs cTnI assay is 1-2 pg/mL with $99^{th}$ percentile value for a healthy population for this assay of 26 pg/ml (16 pg/mL for females and 34 pg/mL for males). Per the package insert, the lower limit of detection (LLoD) is 1 pg/mL with a lower limit of quantification (LLoQ, ≤0% coefficient of variation) of 5 pg/mL. Research reagents for hs cTnI will be provided by Abbott Diagnostics Medical Affairs group.

FABP3 Assay:

FABP3 levels in EDTA plasma will be determined using an ELISA kit purchased from R&D Systems (Duoset ELISA Cat # DY1678). We have considerable recent experience with this assay which employs biotinylated detection antibody visualized with Streptavidian-HRP and TMB substrate (Sigma Cat T0440). Optical density is read on a BioTek Synergy MX at 450 nm with data analysis using BioTek Gen5 software and a four parameter logistic curve-fit. This assay has been validated with spike recovery and dilutional linearity of spiked and high endogenous protein samples. The a LLoD of 0.2 ng/ml with an LLoQ of 4.5 ng/ml. This assay is not approved for clinical use and $99^{th}$ percentile values have not been established. Plasma levels of 15.6±8.5 ng/mL (Mean±SEM) were obtained from a group of 50 healthy subjects (range 2.9-24.5 ng/ml).

MYL3 Assay:

Ventricular myosin light chain (MYL3) will be determined using a conventional sandwich ELISA recently developed by us. This assay uses commercially available anti-MYL3 antibodies (mouse monoclonal Biospacific #2-018-C for capture; and goat polyclonal Biospacific # G-122-C for detection) and MYL3 protein (Origene TP303122). Donkey anti-Goat HRP-conjugated IgG (Jackson Immunochemical) and TMB substrate are used for visualization. Optical density is read on a BioTek Synergy MX at 450 nm and data analyzed using BioTek Gen5 software and a four parameter logistic curve-fit. The assay was validated with spike recovery and dilutional linearity with a LLoD of 0.3 ng/ml and a LLoQ of 4.5 ng/ml. This is a proprietary assay which is not commercially available and $99^{th}$ percentile values have not been established. Plasma levels of 1.9±12 ng/ml (Mean±SEM) were obtained from a group of 50 control subjects (range ≤0.3 to 13.9 ng/ml).

Comparison of Early Biomarker-Time Profiles Following Ischemic MI and Following PTSMA:

The information from patients obtained at the time of plasma sample collection will establish the time that has elapsed since the onset of MI symptoms in relation to sample collection. Comparisons of biomarker levels and changes will then be made between 3 subgroups of +MI patients based on time since MI symptom onset prior to the first (time 0) sample: subgroup 1, symptom onset <2 h prior to collection of first sample; subgroup 2, symptom onset 2-4 h prior to first sample collection; and subgroup 3, symptom onset ≥4 h prior to first sample collection. We estimate that approximately 15-20% of patients will fit criteria for subgroup 1, providing the minimum number needed (10-12 patients) in this subgroup for analysis. Biomarker levels and changes at 30 min and 1 hour will be compared for each biomarker between groups using both parametric analyses (ANOVA and post-hoc T-test with Bonferroni correction) and non-parametric analyses (Wilcoxon Rank Sum) as appropriate. Qualitative and quantitative comparisons will be made to the levels and magnitude of changes during the same time intervals following PTSMA. These analyses will include corrections for relative size of MI based on available peak cTnI data from the +MI cohort and the PTSMA groups. At the completion of this we will have established levels and time profiles for the three biomarkers at early time points following ischemic MI. We will also have determined whether changes in these biomarkers following ischemic MI are similar to those following PTSMA. These studies will provide considerable insight into similarities and differences between the PTSMA model and ischemic MI. This will help guide future exploration of ischemic MI biomarkers in the PTSMA model.

What is claimed is:

1. A method to detect an acute cardiovascular syndrome or disorder in a subject, the method comprising:
   a) detecting a level of cardiac troponin I (cTnI), fatty acid binding protein (FABP3) and ventricular myosin alkali light chain (MYL3) in a first, second and third biological sample obtained from the subject about 30 minutes apart;
   b) comparing the level of cTnI, FABP3 and MYL3 detected in (a) to a reference level and comparing the level of cTnI, FABP3 and MYL3 between the first, second and third biological samples;
   c) identifying the subject as having an acute cardiovascular syndrome or disorder when the level of cTnI, FABP3 and MYL3 is significantly increased relative to the reference level, wherein high levels of FABP3 in combination with the presence of cTnI and MYL3 indicates an acute cardiovascular syndrome or disorder from about 30 minutes to about 15 hrs from onset, wherein high levels mean greater than about 30 ng/ml, and wherein a positive rate of change and a positive change in the rate of change in cTnI, a positive rate of change in FABP3, and a positive then negative change in the rate of change in FABP3 indicates an acute cardiovascular disorder <4 hrs from onset; and
   d) administering treatment to the identified subject of step c, wherein the treatment is one or more of antiplatelet agents, aspirin, clopidogrel, supplemental oxygen, nitrates, pain medication, beta blockers, metoprolol, atenolol, carvedilol, unfractionated heparin, low-molecular-weight heparain, dalteparin, enoxaparin, warfarin, fibrinolytics, angiotensin-converting enzyme inhibitors, angiotensin receptor blockers, captopril, Ramipril, Lisinopril, glycoprotein IIb/IIIa antagonists, abciximab, eptifibatide, tirofiban, statin therapy, aldosterone antagonists, percutaneous coronary intervention, surgical revascularization or implantable cardiac defibrillators.

2. The method of claim 1, wherein the biological sample is a blood sample.

3. The method of claim 1, wherein the acute cardiovascular syndrome or disorder comprises coronary artery disease, atherosclerosis, acute myocardial injury, arteriosclerosis, unstable angina pectoris, embolism, deep vein thrombosis, stroke, congestive heart failure or arrhythmia.

4. The method of claim 3, wherein the acute cardiovascular syndrome or disorder is acute myocardial injury.

5. The method of claim 1, wherein the subject is at risk of developing an acute cardiovascular syndrome or disorder.

6. The method of claim 1, wherein the level of cTnI, FABP3 and MYL3 is indicative of the time that has elapsed since onset of the acute cardiovascular syndrome or disorder.

7. The method of claim 1, wherein the method is repeated at intervals to determine the change in level of cTnI, FABP3 and MYL3 in the biological sample over time.

8. The method of claim 7, wherein the subject is monitored for the progression of the acute cardiovascular syndrome or disorder.

9. The method of claim 1, wherein the level of cTnI, FABP3 and MYL3 is compared to a profile of cTnI, FABP3 and MYL3 to indicate the duration of the acute cardiovascular syndrome or disorder.

10. The method of claim 1, wherein the level of cTnI, FABP3 and MYL3 are detected by an immunoassay; an enzyme linked immunoassay (ELISA); fluorescence based assay; dissociation enhanced lanthanide fluoroimmunoassay (DELFIA), radiometric assay, multiplex immunoassay; cytometric bead assays or combinations thereof; and sensors.

11. The method of claim 1, wherein the level of cTnI, FABP3 and MYL3 is detected by mass spectrometry.

* * * * *